504-371 EX
XR RE 26,912
BEST AVAILABLE COPY

3367333

June 23, 1970 S. C. SCHEIER Re. 26,912

PILE DIAPER

Original Filed July 12, 1965 5 Sheets-Sheet 1

INVENTOR:

STANLEY C. SCHEIER

BY Parrott, Bell, Seltzer, Park & Heard

ATTORNEYS

PILE DIAPER

Original Filed July 12, 1965 5 Sheets-Sheet 2

INVENTOR:
STANLEY C. SCHEIER

BY Garrett, Bell, Seltzer, Park & Heard

ATTORNEYS

PILE DIAPER

Original Filed July 12, 1965 5 Sheets-Sheet 3

INVENTOR:
STANLEY C. SCHEIER

BY Barrett, Bell, Seltzer, Park & Gwynn
ATTORNEYS

PILE DIAPER

Original Filed July 12, 1965 5 Sheets-Sheet 4

INVENTOR:
STANLEY C. SCHEIER
BY Barrett, Bell, Seltzer, Park & Heard
ATTORNEYS

PILE DIAPER
Original Filed July 12, 1965 5 Sheets-Sheet 5
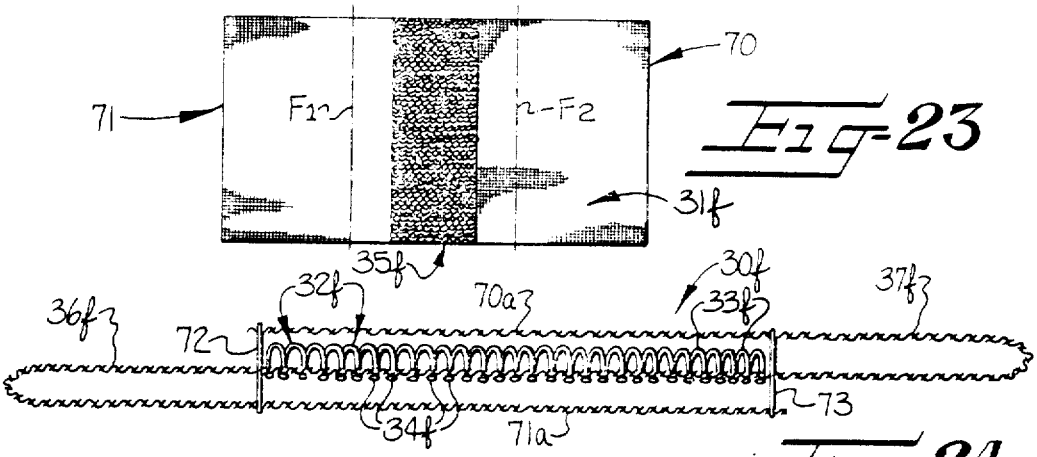
Fig-23
Fig-24
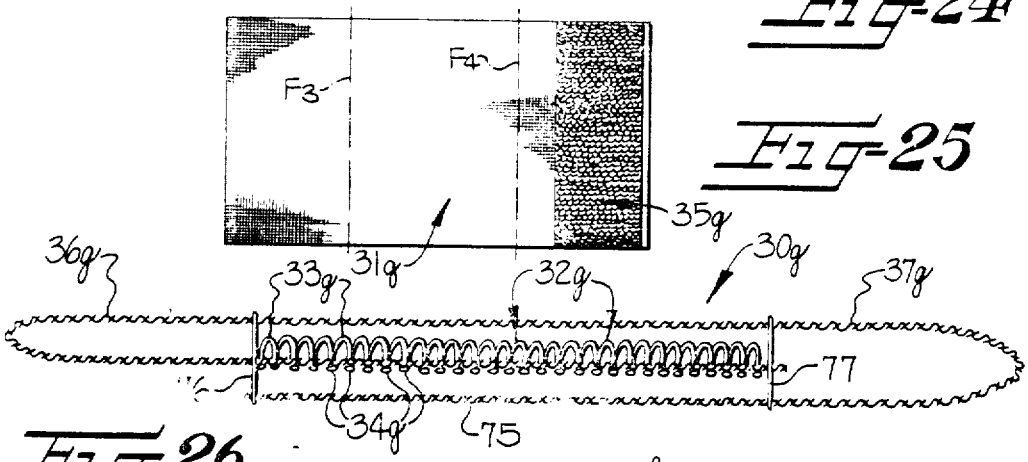
Fig-25
Fig-26
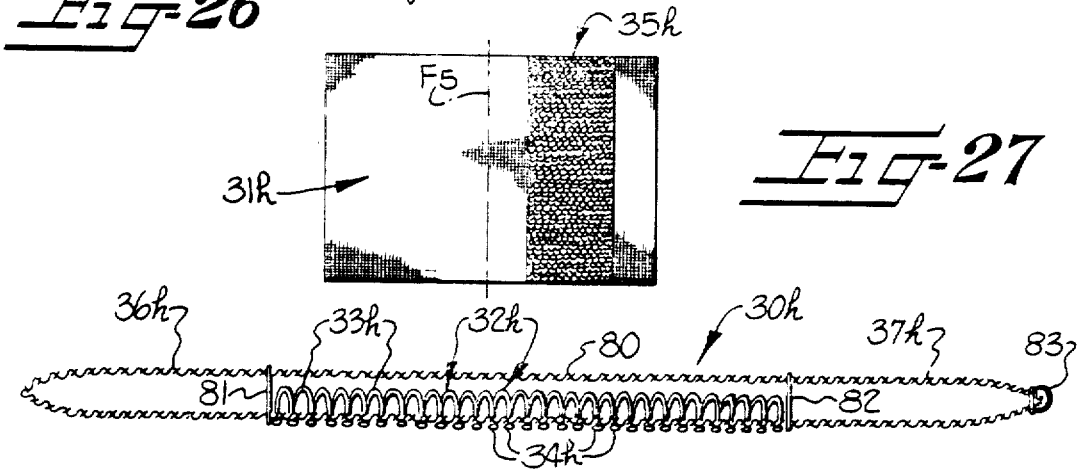
Fig-27
Fig-28
INVENTOR:
STANLEY C. SCHEIER
BY Barrett, Bell, Seltzer, Park & Gaard
ATTORNEYS United States Patent Office Re. 26,912
Reissued June 23, 1970

26,912
PILE DIAPER

Stanley C. Scheier, East Greenwich, R.I., assignor to The Kendall Company, Boston, Mass., a corporation of Massachusetts Original No. 3,367,333, dated Feb. 6, 1968, Ser. No. 471,216, July 12, 1965. Application for reissue Apr. 24, 1969, Ser. No. 824,010
Int. Cl. A61f *13/16*
U.S. Cl. 128—284 20 Claims

Matter enclosed in heavy brackets [ ] appears in the original patent but forms no part of this reissue specification; matter printed in italics indicates the additions made by reissue.

The present invention relates to diapers and more particularly to improved diapers having at least one pile portion or area and other portions or areas devoid of pile, which portions are constructed and arranged to provide highly desirable diaper characteristics or features, such as increased absorbency, softness, and/or wearer comfort, not heretofore provided by conventional diapers.

It is well known that absorbency, softness, wearer comfort and the like are highly desirable characteristics or features for a diaper. Also, it is well recognized that greater absorbency is needed in a central portion of a diaper than in the remaining portions thereof. With this in mind, it is common practice to fold conventional diapers in such a manner that a greater number of fabric layers are provided in the central portion than in other portions to provide the desired absorbency therein. This practice is particularly prevalent with diapers of the prefold type which are folded to a size adapted to fit an infant and stitched in folded condition by the diaper manufacturer. While providing the desired greater absorbency, the greater number of fabric layers in the central portion of these diapers create certain problems in use, such as increased bulkiness between the infant's legs.

Various other constructions have been proposed to provide the greater absorbency in the central portion of the diaper. One such approach has proposed the provision of either permanently attached or removable diaper liners or pads. These liner or pad constructions suffer from the aforementioned problems to an even greater extent than conventional diapers and, in addition, are expensive to manufacture and bothersome to use.

It has also been proposed that a diaper could be constructed of woven terry fabric in an attempt to provide the desired absorbency in the central portion of the diaper while obviating the problems encountered with the conventional diaper as described above. However, such woven terry fabrics are formed by a special weaving process wherein both a ground warp and a pile warp are utilized and the pile yarns are woven as an integral part of the ground fabric. Therefore, the ground or base must be a woven fabric of interwoven warp and filling yarns and other possibily desired ground or base materials may not be used. Also, the pile yarns must have sufficient twist therein to withstand the stresses thereon during weaving of such yarns in the fabric and this relatively high twist results in increased harshness and reduced absorbency in the pile surface. Thus, terry fabrics cannot provide the desired softness and absorbency in a diaper. For these reasons as well as other reasons incident to the nature of the special weaving process required to produce terry fabric, pile diapers of terry fabric have not been commercially accepted in this country.

Further, the discomfort of the wearer due to the lingering presence of a moisture laden or wet surface in contact with the wearer's skin has given rise to various diaper constructions which attempt to provide increased wearer comfort by utilizing a hydrophobic portion adapted to contact the wearer's skin to wick the moisture therefrom and a hydrophilic portion disposed away from the wearer's skin to absorb the moisture being wicked away by the hydrophobic portion. Since the hydrophobic portion does not absorb the moisture, a drier surface is provided against the wearer's skin which enhances the comfort of the wearer and inhibits the formation of certain skin maladies, such as diaper rash.

With previous constructions of this type, it is common practice to utilize special weaves to provide woven fabrics having hydrophobic yarns predominately on one surface and hydrophilic yarns predominately on the other surface thereof. With such previous diapers, it has not been possible to obtain the desired absorbency in the diaper and this is particularly true with respect to the central portion of the diaper.

It is, therefore, an object of the present invention to provide a pile diaper obviating the aforementioned problems and deficiencies of conventional diapers and previously proposed pile diapers by providing the desired softness and absorbency without relying upon folding to provide an increased number of layers in the central portion, inserts or pads, or special weaves.

A more specific object of this invention is to provide a pile diaper wherein the base and/or pile yarns may be formed of a wide variety of materials for achieving diaper characteristics, such as a high degree of absorbency, softness and wearer comfort, not heretofore achievable in diapers.

A further more specific object of the present invention is to provide a pile diaper wherein the pile is anchored in the base without being interwoven therewith to prevent any weakening of the base upon any damage to the pile.

A still more specific object of this invention is to provide a pile diaper wherein pile yarns may be utilized of such low twist as to be impractical for use in woven pile fabrics, such as terry fabrics, but very desirable for use in diapers due to the increased softness and/or absorbency thereof.

Another object of the present invention is to provide a pile diaper having hydrophobic and hydrophilic characteristics for increased wearer comfort without relying upon special weaves, and wherein the desired absorbency, particularly in the central portion of the diaper, is provided.

Some of the objects of the invention having been stated, other objects will appear as the description proceeds when taken in connection with the accompanying drawings in which:

FIGURE 23 is a plan view of a diaper blank adapted to be formed into a further modified form of diaper in accordance with the present invention;

FIGURE 24 is an enlarged transverse sectional view of the finished diaper formed from the diaper blank shown in FIGURE 23;

FIGURE 25 is a plan view similar to FIGURE 23 of another diaper blank adapted to be formed into another modified form of diaper embodying the features of the present invention;

FIGURE 26 is an enlarged transverse sectional view of the finished diaper formed from the diaper blank shown in FIGURE 25;

FIGURE 27 is a plan view similar to FIGURES 23 and 25 of still another diaper blank adapted to be formed into a still further form of diaper in accordance with this invention; and FIGURE 28 is an enlarged transverse sectional view of the finished diaper formed from the diaper blank shown in FIGURE 27.

Figure 1:
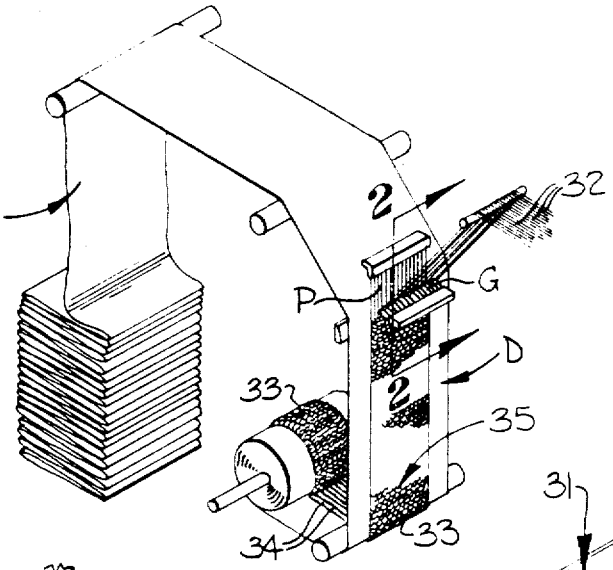
FIGURE 1 is a generally schematic view illustrating the manner of forming a web of diaper material in accordance with the present invention from which finished diapers may be formed.
Figure 3:
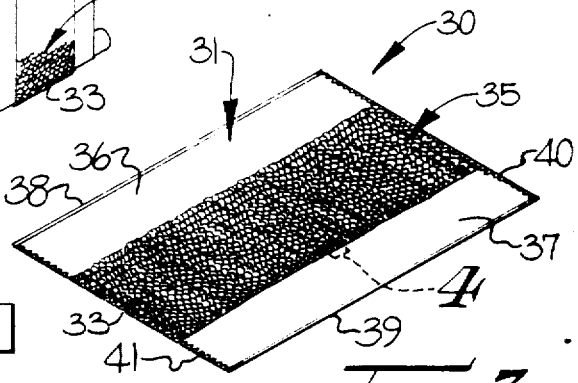
FIGURE 3 is an isometric view of a finished diaper incorporating the features of the present.

Generally, the present invention contemplates several forms or embodiments of diapers which are characterized by at least one pile portion or area and other portions or areas devoid of pile, which diapers are constructed and arranged to provide highly desirable diaper features or characteristics, such as increased absorbency, softness, and/or wearer comfort, not heretofore provided by conventional diapers. The diapers of the present invention are preferably formed by first forming a web of diaper material D (FIGURE 1) which is then transversely severed into diaper blanks. The diaper blanks are then formed into the finished diapers, such as diaper 30 (FIGURE 3), as will be described more fully hereinafter.

In the embodiments illustrated in the drawings, the web of diaper material D (FIGURE 1) is preferably formed on a machine of the type illutstrated in United States Patent No. 3,174,308. The web of diaper material D includes a base web B, which extends throughout the web of diaper material D, and a severed length of which forms the base of a diaper of the present invention, such as base 31 of diaper 30. Pile yarns, such as pile yarns 32 of diaper 30, penetrate through and are anchored within at least one portion of the base web B and form pile, such as pile loops 33 of diaper 30, on one surface thereof and are interknit and form stitch loop chains such as stitch loops 34 of diaper 30, on the other surface thereof. The pile yarns and the at least one portion of the base through which they penetrate cooperate to define at least one pile area in the web of diaper material D which will define a pile area, such as pile area 35 of diaper 30, in the finished diaper.

Figure 2:
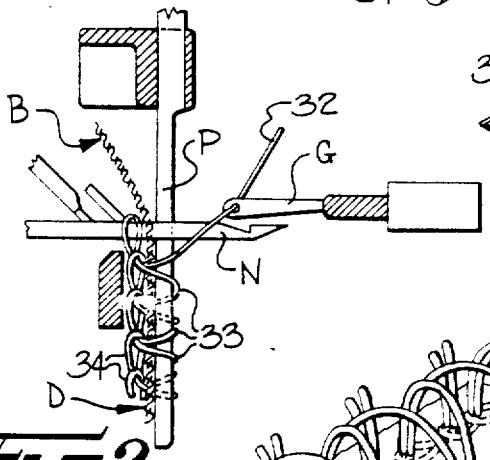
FIGURE 2 is an enlarged fragmentary sectional view taken substantially along line 2—2 in FIGURE 1.

The machine for forming the web of diaper material D by combining the pile yarns with the base web includes a bank of needles N (FIGURE 2), which are of a combined width corresponding to the desired width of the pile area in the web of diaper material and are reciprocated to successively penetrate and be withdrawn from the base web. Needles N are associated with suitable yarn guides G, with a yarn guide being provided for each needle and having a pile yarn threaded therethrough. Pile wires P are disposed between adjacent pairs of needles N and extend generally perpendicular thereto and parallel to the path of travel of the base web as the same is fed past the needles.

Yarn guides G are reciprocated laterally of the base web between adjacent pairs of needles in timed relation to the reciprocation of the needles to move each pile yarn 32, except for the distal yarns 32 in the bank of pile yarns, into position to be caught by the hook portion of first one needle and then the hook portion of another needle in the adjacent pairs of needles so that a pile yarn will be drawn through the base web by first one needle and then another needle at both laterally and longitudinally spaced points upon each reciprocation of the needles. The reciprocation of the yarn guides G between adjacent pairs of needles also results in the pile yarns being shogged back and forth over the pile wires P so that when the needles are withdrawn from the base web, the pile wires hold portions of the pile yarns away from the surface of the web and form the pile which may be either cut or uncut as desired. Of course, the height of the pile may be varied by varying the height of the pile wires P. The portions of the pile yarns which are drawn through the base web upon each withdrawal of the needles N, are held on the needles for one complete reciprocation thereof so that these portions are interknit and form stitch loop chains on the reverse side of the base web from the pile portions.

It is contemplated by the present invention that the base web B may be formed of any pliable material, with the particular material used depending upon the characteristics desired in the finished diaper. Some examples of materials suitable for use as the base web are a pre-woven fabric, a pre-formed non-woven fabric, and a pre-knitted fabric. Further, a fabric of the type illustrated in United States Patent No. 2,890,579 may be utilized as the base web if desired, and in such an event, the machine forming this fabric may be arranged in tandem with the machine forming the web of diaper material. The base web may then be fed directly from one machine into the other machine.

Similarly to the base web B, the pile yarns may also be of any desired material depending upon the characteristics desired in the pile area of the finished diaper. In this respect if softness and absorbency are the characteristics desired in the pile area of the finished diaper, the pile yarns should be formed of a hydrophilic material and preferably are formed of water swellable cellulosic material, such as staple vicose rayon. Also, these pile yarns preferably have a size within the range of about 3/1 and 25/1 (cotton count) to provide the degree of absorbency desired and for more complete coverage of the surface of the base web. Due to the special structural character of the pile area of the web of diaper material D, these pile yarns may also have such low twist therein as to make such yarns impractical for use in woven fabrics, such as conventional diaper fabrics or terry fabrics, but which greatly enhances both the softness and absorbency of the pile area of the finished diaper. In this respect, the pile yarns for the diapers of this invention preferably have a twist multiple (turns per inch divided by the square root of the yarn size) of no more than 3.5 which is below the standard twist multiples for diaper fabrics.

Figure 4:
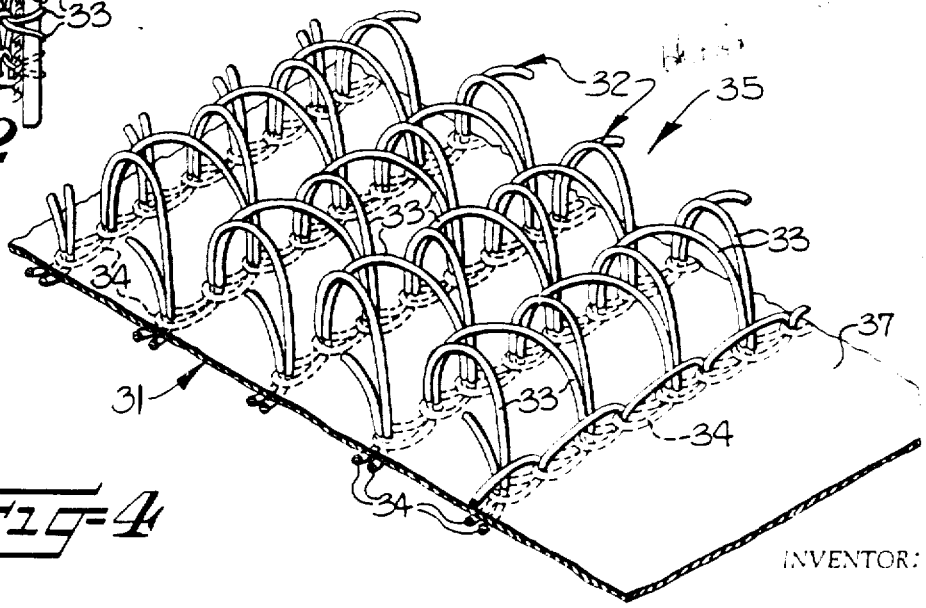
FIGURE 4 is a partially schematic, enlarged fragmentary perspective view of the portion of diaper enclosed in the rectangle 4 in FIGURE 3.

Turning now to a consideration of the illustrated forms or embodiments of this invention, diaper 30 (FIGURE 3) includes elongate base 31 which preferably is of single layer construction and which may be of any desired material, such as non-woven fabric of either hydrophobic or hydrophilic fibers. Pile yarns 32 penetrate through a selected portion or area of base 31 and form pile loops 33 on one surface thereof and interknit stitch loops 34 on the other surface to define a pile area 35, which preferably is in the central portion of the base and defines a pile central panel extending between the ends of the diaper and having a width substantially equal to one-half (½) the width of the diaper 30. Due to the manner of formation of pile loops 33 as described above, they are arranged in parallel rows extending lengthwise of the base 31 (FIGURE 4) and are disposed in a zig-zag pattern in each of the rows, with the points of penetration of the base 31 by the leg portions of the pile loops in one row and the proximal leg portions of the pile loops in the adjacent row being aligned longitudinally of the rows and the base.

Base 31 has portions 36 and 37 on opposite sides of the pile central panel 35 which are devoid of pile and which define pinning panels in the finished diaper 30. These pinning portions 36, 37 have outer side edges 38 and 39, respectively, which are finished to prevent fraying or raveling by any suitable means. The cut ends of the diaper 30 which were formed when the same was severed from the web of diaper material are also finished by any suitable means, such as overedge stitching 40, 41.

Figure 16:
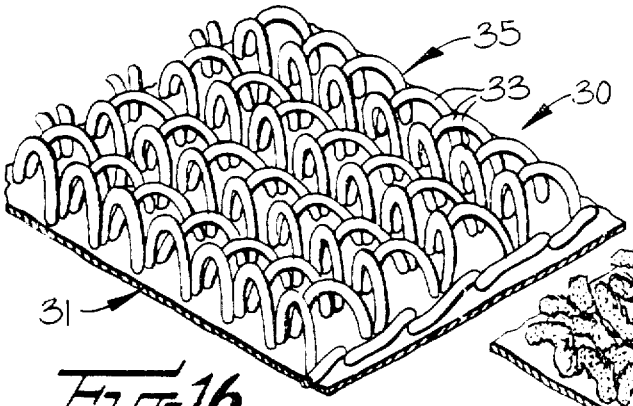
FIGURE 16 is a fragmentary isometric view of the central pile portion of a diaper formed in accordance with the present invention.
Figure 17:
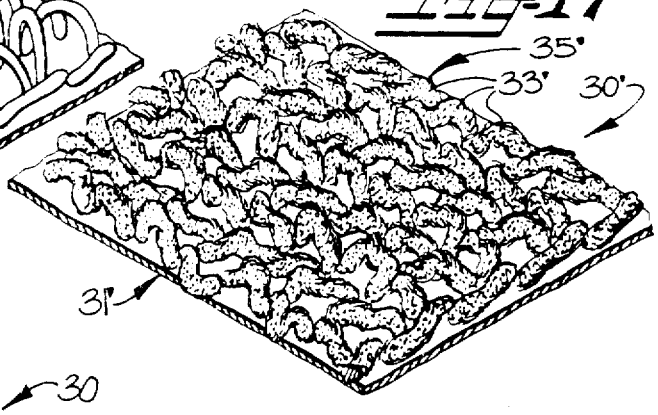
FIGURE 17 is an isometric view similar to FIGURE 16 of a diaper constructed in accordance with the present invention wherein the pile yarns are formed of hydrophilic material and are shown after repeated launderings.

As stated above, pile yarns 32 may be formed of either hydrophobic or hydrophilic material, but in diaper 30, these yarns preferably consist essentially of hydrophilic material for both softness and absorbency. More preferably, pile yarns 32 are formed of water swellable, cellulosic fibers, such as viscose rayon, which will shrink upon repeated launderings. Due to the special construction of the pile central panel 35 of diaper 30, and other diapers produced in accordance with this invention, very special and desirable characteristics are achieved after such repeated launderings. These very desirable characteristics have been illustrated in FIGURES 16 through 19 wherein portions of diaper 30 are shown both before any laundering thereof (FIGURES 16 and 18) and after repeated launderings (FIGURES 17 and 19), e.g., fifteen (15) such launderings.

Figure 18:
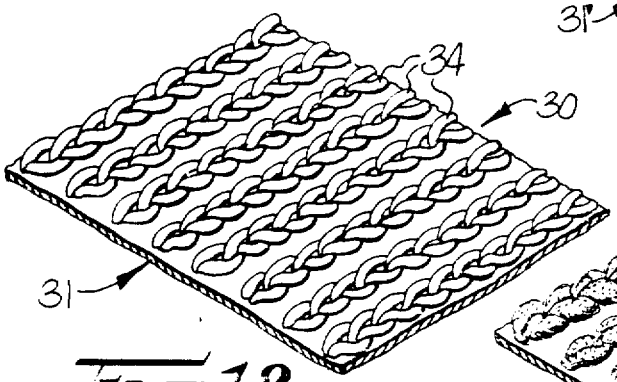
FIGURE 18 is an isometric view of the reverse side of the portion of diaper shown in FIGURE 16.
Figure 19:
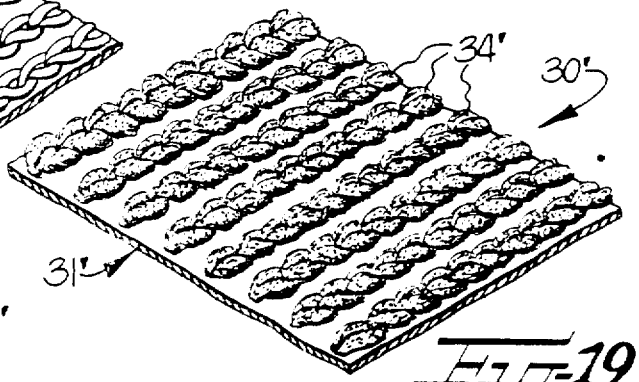
FIGURE 19 is an isometric view of the reverse side of the portion of diaper illustrated in FIGURE 17.
Figure 20:
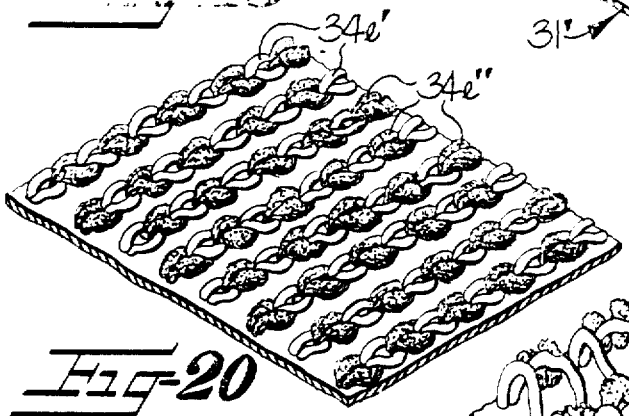
FIGURE 20 is a view similar to FIGURE 19 of a portion of diaper wherein both hydrophobic and hydrophilic yarns have been utilized and showing the effects of repeated launderings upon those two types of yarns.

In this respect, as initially formed, the pile loops 33 are of a rather substantial, common height above the base 31 (FIGURE 16) and the stitch loop chains 34 are relatively tight and lie rather closely against the base 31 (FIGURE 18). Upon such repeated launderings, the cellulosic pile yarns 32 swell and shrink due to the effects of the washing medium and mechanical agitation of the diaper, and the pile loops 33' are drawn closer to the surface of the base 31' and assume a more randomly oriented arrangement and, due at least in part to the yarn shrinkage and swelling and this random arrangement, form a closely matted surface on the base 31'.

In addition, the twist in these yarns has a tendency to relax and the yarns open or blossom-out due to separation of the individual fibers therein. Such opening or blossoming of the pile yarns materially enhances the absorbency and softness thereof and also increases the coverage of the base 31' and contributes to the matted nature of the surface defined by pile loops 33'. Further, if base 31' is formed of cellulosic material, it will also shrink during such launderings and this will result in the pile loops 33' being closer together and will provide greater coverage of the base thereby.

At the same time that the pile loops 33' become shortened or reduced in height, the stitch loops 34' become loosened to provide a more raised surface on this side of the base 31'. Also, the yarn portions defining the stitch loops 34' open or blossom-out to provide a considerably softer, more absorbent, and more compact surface on this side of base 31'. Accordingly, both surfaces of the diaper 30' have the absorbency, softness and compactness thereof considerably enhanced by the launderings to which diapers are invariably subjected.

Figure 5:
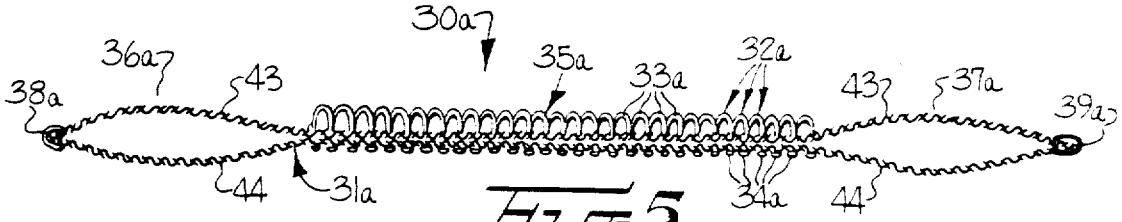
FIGURE 5 is a transverse sectional view of a modified form of diaper embodying the feautres of the present invention.
Figure 6:
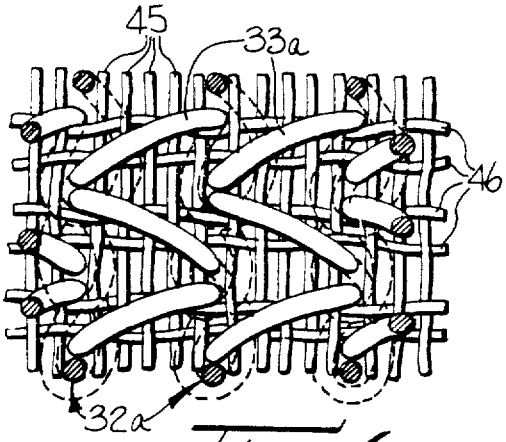
FIGURE 6 is an enlarged fragmentary plan view of the central portion of the diaper shown in FIGURE 5.
Figure 7:
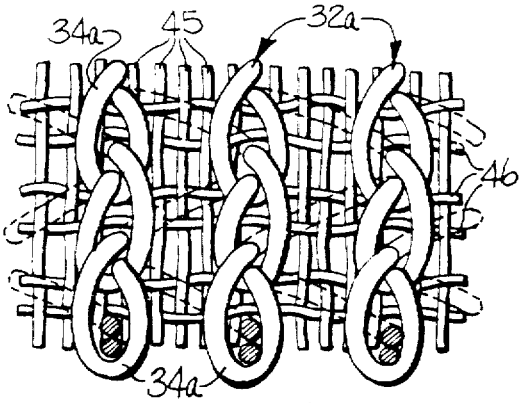
FIGURE 7 is a bottom plan view of the central portion of the diaper shown in FIGURE 5.

Another form of diaper, generally indicated, at 30a is shown in FIGURES 5 through 7 and includes another type of base 31a which comprises a pre-woven fabric, which may be of single or multi-layer construction, but preferably comprises upper and lower diaper layers 43 and 44, each of which includes interwoven sets of warp and filling yarns 45, 46, respectively (FIGURES 6 and 7). It is noted that the multi-layer character of base 31a permits the needles N to more readily penetrate therethrough than through a single layer base of denser construction and rupturing of warp and/or filling yarns in the fabric of the base is reduced or avoided.

Pile yarns 32a penetrate through the central portion of both of the layers 43, 44 in the manner described above and form pile loops 33a on one surface thereof and stitch loops 34a are on the other surface thereof. It is noted that the pile yarns 32a secure the central portion of the two layers together and cooperate therewith to define a pile central panel 31a. Since the leg portions at one side of adjacent pile loops 33a penetrate the base 31a at a common point (FIGURES 6 and 7) and each of the pile loops extend diagonally of the base, all of the filling yarns 46 extend beneath pile loops and there are no filling yarns between adjacent loops in the rows, as in terry fabric. Also, since the points of penetration of proximal leg portions of the pile loops in adjacent rows are aligned, all of the warp yarns 45 extend beneath pile loops 33a and there are no warp yarns between the rows of pile loops as in terry fabric. Accordingly, more complete coverage of base 31a by pile loops 33a may be provided.

Portions of the layers 43, 44 on opposite sides of the pile central panel 35a are devoid of pile and remain independent of each other to define pinning panels 36a, 37a. It is noted that the multi-layer construction of these pinning panels 36a, 37a and the independent nature of such layers facilitate the insertion of pins therethrough for ease in pinning the diaper on the wearer. The side edges 38a, 39a and ends (not shown) are secured together and finished, as by over-edge stitching to prevent raveling and/or fraying.

The fabric layers 43 and 44 may be woven in any desired weave design to provide the desired strength, softness, and pliability in base 31a. Examples of weave designs which have been used in producing diapers in accordance with this invention are a plain weave design, with a fabric construction in the range of conventional gauze diaper fabric, and a birdseye weave design, with fabric construction also within the range of conventional birdseye diaper fabric.

Figure 11:
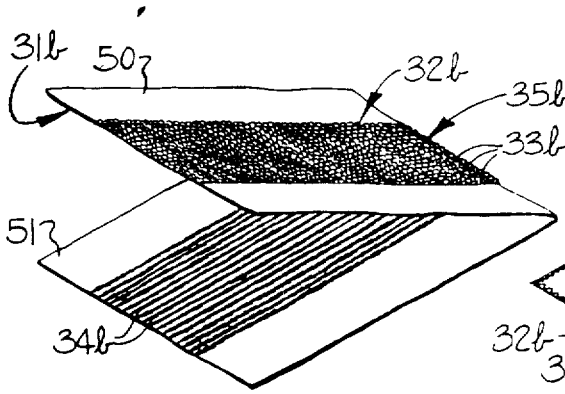
FIGURE 11 is an isometric view of a modified form of diaper of the present invention having a pile face on opposite outer surfaces thereof, and illustrating the manner of folding thereof.
Figure 12:
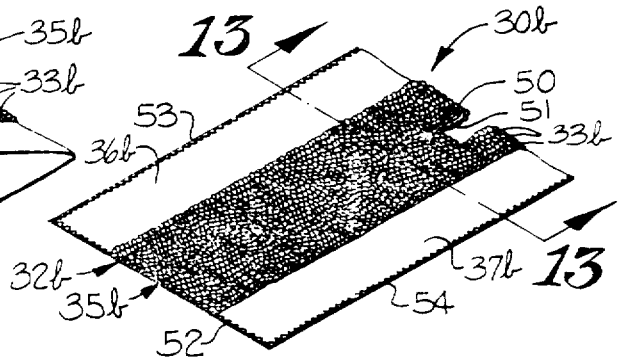
FIGURE 12 is an isometric view of a finished form of the diaper shown in FIGURE 11 with a portion broken away to illustrate the folded edge.
Figure 13:
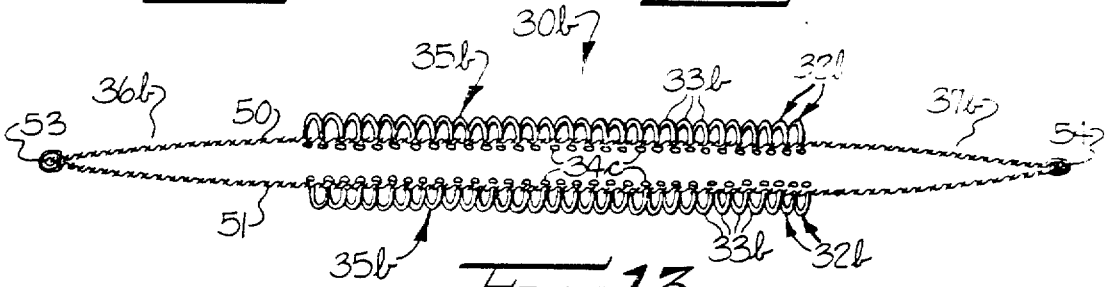
FIGURE 13 is an enlarged transverse sectional view taken substantially along the line 13—13 in FIGURE 12.

A third form of diaper, generally indicated at 30b, is shown in FIGURES 11 through 13 and differs from the above-described diapers 30 and 30a primarily in that a pile face is provided on opposite outer surfaces thereof. Diaper 30b includes an elongate base 31b preferably comprising a single layer of pre-woven textile fabric having pile yarns 32b penetrating through a medial portion thereof and forming pile loops 33b on one surface thereof and interknit stitch loops 34b on the other surface thereof and defining therewith a pile central panel 35b extending between the ends of the base 31b.

Diaper 30b is formed by severing the web of diaper material defined by the base web and the pile yarns at spaced points corresponding to twice the desired length of the finished diaper. This severed length of diaper material or diaper blank is then folded about a medial transverse fold line to form superposed upper and lower diaper sections 50 and 51, each of which have pile yarns 32b penetrating through the central portion thereof. The pile loops 336b on each section are disposed on the outer surface thereof and the stitch loops 34b are disposed on the interior surface thereof so that the pile central panel 35b has a pile face on opposite outer surfaces thereof (FIGURE 13).

Upper and lower sections 50 and 51 are preferably secured in their superposed relation as by overedge stitching 52 across the end thereof opposite the fold line and overedge stitching 53 and 54 along opposite side edges thereof. The sections 50 and 51 are therefore independent throughout except at the fold line and the end and side edges thereof which provides greater pliability and facilitates insertion of pins through the side portions of the upper and lower sections 50 and 51 of base 31b which define pinning panels 36b and 37b.

Figure 14:
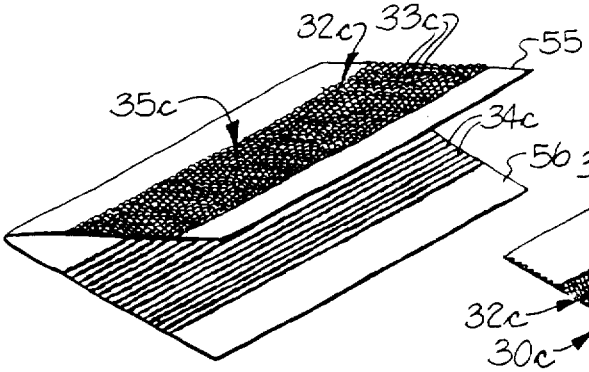
FIGURE 14 is an isometric view similar to FIGURE 11 of another form of diaper having pile faces on opposite surfaces thereof and illustrating the manner of folding thereof.
Figure 15:
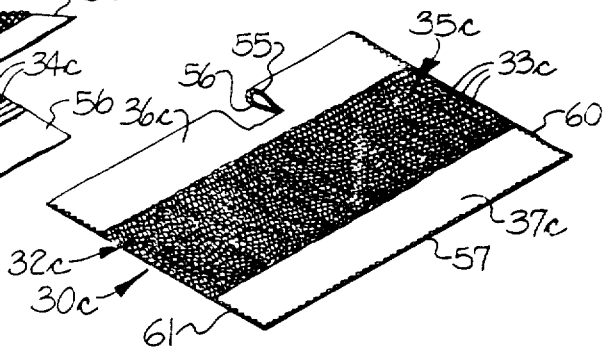
FIGURE 15 is a view similar to FIGURE 12 and illustrating a finished form of the diaper shown in FIGURE 14 with a portion broken away to illustrate the folded edge thereof.

A fourth diaper form, generally indicated at 30c, is shown in FIGURES 14 and 15 and is similar to diaper 30b described above, differing therefrom mainly in the manner of the folding of the diaper blank to form the finished diaper. To produce this diaper, a base web having a width twice the desired width of the finished diaper is provided, as are two banks of pile yarns 32c. Two spaced apart banks of needles N are utilized with these pile yarns to form two spaced apart pile areas or portions extending longitudinally of the base web. The thusly formed web of diaper material is then severed at spaced points corresponding to the desired length of the finished diaper to form a diaper blank.

This diaper blank is folded about a longitudinal medial fold line to provide superposed upper and lower sections 55, 56, each of which have pile yarns 32c penetrating through the medial portion thereof and forming pile loops 33c on one surface thereof and stitch loops 34c on the other surface thereof. The pile loops 33c on each section are disposed on the outer surface thereof and the stitch loops 34c are disposed on the interior surface thereof so that pile central panel 35c defined by these medial portions has a pile face on the opposite outer surfaces thereof. Upper and lower sections 55 and 56 are preferably secured in their superposed relation as by overedge stitching 57 along the side edge thereof opposite the folded edge and overedge stitching 60 and 61 across opposite ends thereof.

The structural characteristics of the diapers of the present invention render the same especially well suited for the use of combinations of hydrophobic and hydrophilic materials, which diapers not only possess the desired absorbency characteristics but also provide increased wearer comfort. In this respect, at least the skin-contacting surface of the diapers should be formed of the hydrophobic material so that the same will wick moisture away from the wearer's skin or remove this moisture from the wearer's skin by capillary action. Other portions of the diaper should be formed of the hydrophilic material and should be arranged relative to the hydrophobic portion or portions so as to absorb the moisture being wicked away from the wearer's skin by the hydrophobic portions and to reain this moisture away from the wearer's skin to provide the increased comfort for the wearer and to inhibit the formation of diaper rash.

Figure 8:
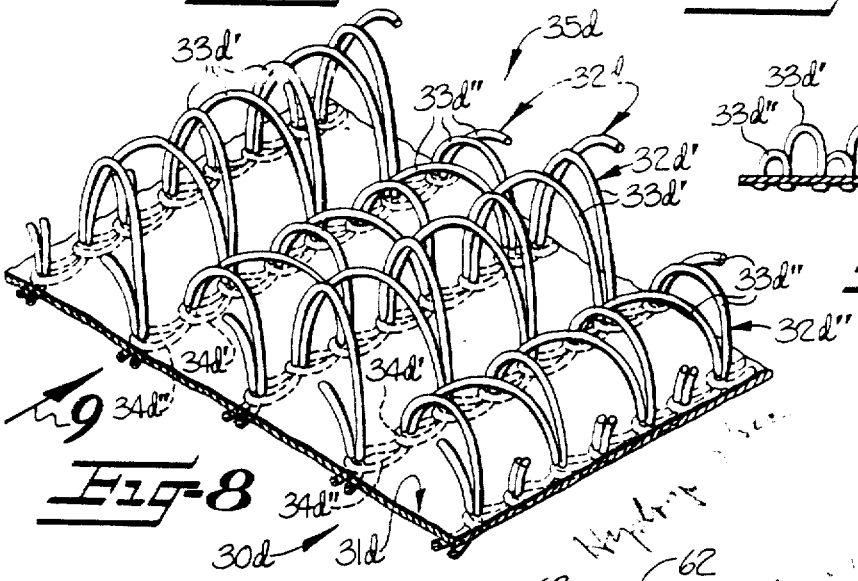
FIGURE 8 is a view similar to FIGURE 4 illustrating still another form of diaper constructed in accordance with the present invention.
Figure 9:
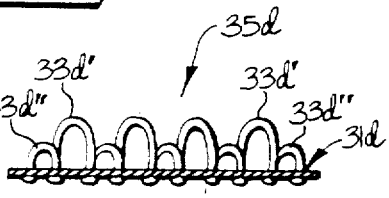
FIGURE 9 is a reduced end elevational view looking in the direction of the arrow 9 in FIGURE 8.

Several forms of diapers utilizing this combination of materials are illustrated, the first of these being a diaper, generally indicated at 30d, shown in FIGURES 8 and 9. This diaper 30d includes a base 31d, which may correspond generally to the base of any of the preceding diapers, and pile yarns 32d penetrating through the base. Certain of the pile yarns 32d' are formed of hydrophobic material, such as polypropylene or nylon, and the other pile yarns 32d'' are formed of hydrophilic material, such as viscose rayon or cotton. Preferably, hyprophobic pile yarns 32d' form pile loops 33d' of a height greater than the height of pile loops 33d'' formed by hydrophilic pile yarns 32d''. In the embodiment illustrated in the drawings, hydrophobic pile yarns 32d' and hydrophilic pile yarns 32d'' are arranged in alternation in the bank of pile yarns and hydrophobic pile loops 33d' form alternate rows of pile loops in pile central panel 35d' and hydrophilic pile loops 33d'' form intervening rows therein or vice versa. Due to the interknitting of the stitch loop portions of the pile yarns, hydrophobic stitch loops 34d' form alternate stitch loops in each stitch loop chain and hydrophilic stitch loops 34d'' form intervening stitch loops therein. By this arrangement, the higher hydrophobic pile loops 33d' define the skin-contacting surface of the pile face on the pile central panel 35d and will serve to wick moisture away from the skin of the wearer. The lower hydrophilic pile loops 33d'' will absorb the moisture being wicked away from the skin by the hydrophobic pile loops 33d' such that the moisture is collected away from the skin of the wearer.

In certain instances, it may be desirable to utilize core-spun yarns as the hydrophilic pile yarns 32d'' wherein a strong core, such as continuous filament, has a sheath of the hydrophilic fibers spun therearound. Such core-spun yarns would provide greater strength and wearability than yarns formed entirely of the hydrophilic fibers, and in addition, such core-spun yarns would provide a means of controlling shrinkage of the hydrophilic pile yarns upon repeated launderings to better maintain the hydrophilic pile loops 33d'' closer to the height of the hydrophobic pile loops 33d'.

The above described hydrophobic and hydrophilic high-low pile may be obtained with a diaper material wherein the differential shrinkage characteristics of the hydrophobic pile yarns and hydrophilic pile yarns upon repeated launderings provide pile loops of different height from pile loops which were initially of the same height. In such a diaper construction, the hydrophobic pile yarns are preferably used to form alternate rows of pile loops and the hydrophilic pile yarns are preferably used to form intervening rows of pile loops.

Figure 21:
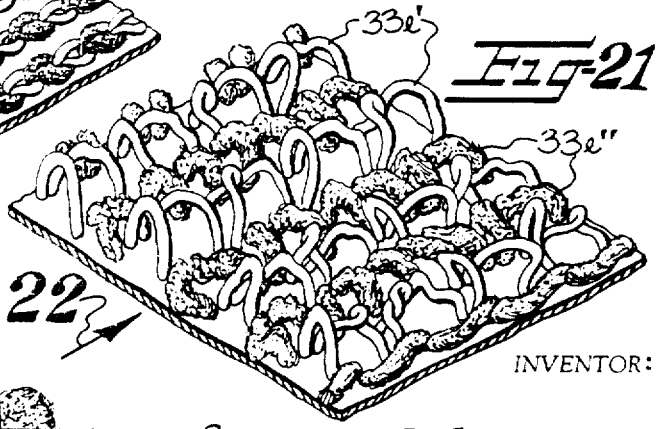
FIGURE 21 is an isometric view of the reverse side of the fabric shown in FIGURE 20.
Figure 22:
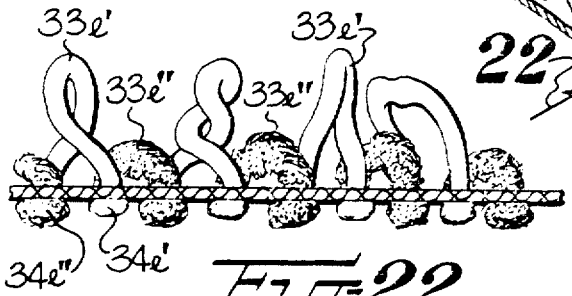
FIGURE 22 is an enlarged end elevational view of the diaper shown in FIGURE 21 looking in the direction of arrow 22 therein.

Upon repeated launderings, the hydrophilic pile yarns will swell, open or blossom-out, and shrink so that the hydrophilic pile loops 33e'' (FIGURES 21 and 22) will become of reduced height and of increased size or diameter to more completely fill the spaces between the hydrophobic pile loops 33e'. In contrast thereto, the hydrophobic pile loops 33e' will not swell, open or shrink to any appreciable extent. The laundering conditions have some effect upon the hydrophobic pile loops 33e' and this effect manifests itself in a tendency of the hydrophobic pile loops 33e' to assume irregular shapes and positions with respect to the base 31e'. These positions may include a twisting of the pile loops upon themselves, in a flattening out of the pile loops, and/or in the pile loops becoming tilted over with respect to the base (FIGURES 21 and 22). Even with this effect upon the hydrophobic pile loops, however, the hydrophobic pile loops 33e' still remain at a higher elevation than the hydrophilic pile loops 33e'' such that the hydrophobic pile loops 33e' will contact the skin of the wearer and wick moisture away from the wearer's skin to be absorbed by the hydrophilic pile loops 33e'' disposed away from the skin of the wearer.

The swelling, shrinkage and opening of the hydrophilic pile yarns upon launderings also results in the stitch loops 34e'' formed thereby becoming loosened and more open or blossomed-out. This provides a softer, more comfortable surface on this side of the diaper. In contrast to the hydrophilic stitch loops 34e'', the hydrophobic stitch loops 34e' remain rather tight and close to the surface of the base which contributes to the pile loops 33e' being of a greater height than pile loops 33e''.

Figure 10:
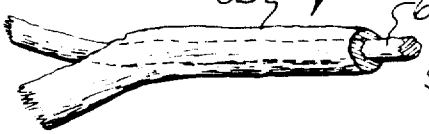
FIGURE 10 is a fragmentary view of a section of core-spun yarn adapted to be used in another form of diaper constructed in accordance with the present invention.

Alternatively, the above-mentioned hydrophobic and hydrophilic features may be obtained in the pile area of a diaper formed in accordance with the present invention by the use of a core-spun yarn 62 (FIGURE 10) as each of the pile yarns. This yarn 62 comprises a sheath 63 of suitable hydrophobic fibers spun around a core 64 of hydrophilic fibers. When yarns 62 are utilized as pile yarns in the pile area of a diaper of this invention and particularly wherein the pile yarns are disposed on the outer surface thereof, the hydrophobic sheaths 63 will serve to wick moisture away from the wearer's skin into the interior of the yarns where this moisture is absorbed by the hydrophilic cores 64. Accordingly, the comfort of the wearer of such a diaper is materially increased since no wet surface remains in engagement with the skin and diaper rash and other skin maladies are inhibited.

In FIGURES 23 through 28, there are shown three additional modified forms of the diapers of the present invention which provide the above described hydrophobic and hydrophilic characteristics. The first form of diaper is shown in FIGURES 23 and 24 and is indicated generally at 30f. Diaper 30f includes a base 31f which is preferably in the form of a single layer of pre-woven fabric and, when in web form, preferably has a width equal to about two and one-half (2½) times the desired width of the finished diaper. Base 31f consists essentially of hydrophobic material and preferably both the warp and filling yarns thereof are formed of hydrophobic fibers.

Pile yarns 32f penetrate through an intermediate area of the base 31f and form pile loops 33f on one surface thereof and stitch loops 34f on the other surface thereof. The pile yarns 32f cooperate with the portion of the base 31f through which the same penetrate to define a pile area 35f which extends throughout the length of the diaper 30f and is of a width corresponding to the desired width of the central portion of the finished diaper. Pile yarns 32f consist essentially of hydrophilic material and preferably are formed of water swellable cellulosic material, such as viscose rayon, to provide a high degree of absorbency in the central portion of the finished diaper.

Base 31f has portions 70 and 71 on opposite sides of the pile area 35f and these portions are folded about fold lines $F_1$ and $F_2$ which are spaced apart a distance corresponding to the desired width of the finished diaper 30f, in generally an S-type fold. Portion 70 of the base 31f is folded over into superposed relation to the surface of pile area 35f having stitch loops 33f thereon and portion 71 is folded over into superposed relation to the surface of pile area 35f having stitch loops 34f thereon. Accordingly, the central portion of the diaper is formed in three superposed sections with a portion 70a of portion 70 of the base defining one outer or the upper section, a portion 71a of the portion 71 of the base defining the other outer or lower section, and pile area 35f defining the inner section. Superposed portions 70b, 70c and 71b, 71c of the respective portions 70 and 71 on opposite sides of the central portion define pinning panels 36f, 37f respectively. The diaper 30f is preferably secured in the folded condition by spaced lines of stitching 72 and 73 which preferably penetrate through the three sections of the central portion immediately adjacent opposite sides of the pile area 35f.

The second form of diaper is illustrated in FIGURES 25 and 26 and is generally indicated at 30g. Diaper 30g comprises a base 31g which is very similar in construction and dimensions to base 31f described above. In this respect, base 31g consists essentially of hydrophobic material and preferably both the warp and filling yarns thereof are formed of hydrophobic fibers. Pile yarns 32g penetrate through an area of the base 31g immediately adjacent one side thereof, when the same is in base web form, and form pile loops 33g on one surfaece thereof and stitch loop chains 34g on the other surface thereof. As in diaper 30f, the pile yarns 32g consist essentially of hydrophilic material and preferably these yarns are formed of water swellable cellulosic material, such as viscose rayon, to provide the desired absorbency in the diaper 30g.

The diaper blank from which diaper 30g is formed is folded about two spaced fold lines $F_3$ and $F_4$ which are disposed a distance apart corresponding to the desired width of the finished diaper. With this type of fold, the pile area 35g is first moved into superposed relation to the central portion 74 of the base, and the other side portion 75 of the base is then moved into superposed relation to the pile area 35g whereby the pile area is disposed between the portions 74 and 75 of the base. The diaper 30g is secured in folded relation by spaced lines of stitching 76, 77 which preferably penetrate through the three sections of the central portion of the diaper immediately adjacent opposite sides of the pile area 35g. The portions of the base on opposite sides of the central portion are formed of two layers of the base 31g and define pinning panels 36g, 37g, respectively.

Diapers 30f and 30g therefore have central portions which have the opposite outer surfaces thereof formed by portions of the hydrophobic bases while the interior thereof is formed by the pile areas with the hydrophilic pile yarns. Accordingly, when these diapers are applied to the wearer, the hydrophobic portion in contact with the wearer's skin wicks moisture therefrom into the interior of the central portion where the same is absorbed by the pile yarns.

The third form of these diapers is illustrated in FIGURES 27 and 28 and is generally indicated at 30h. This diaper comprises a base 31h formed similarly to the bases 31f and 31g except that when the same is in web form it has a width only twice the desired width of the finished diaper. As with other bases, however, base 31h consists essentially of hydrophobic material and preferably has both the warp and filling yarns formed of hydrophobic fibers.

Pile yarns 32h penetrate through an intermediate area of the base with one side edge of the pile area 35h being spaced from one side edge of the base 31h a distance corresponding to the desired width of the pinning portions of the finished diaper. Pile yarns 32h form pile loops 33h on one surface of the area of the base through which the same penetrate, and stitch loop chains 34h on the other surface thereof. These pile yarns consist essentially of hydrophilic material and preferably are formed of water swellable celluosic material, such as viscose rayon.

The base 31h is folded about a medially disposed fold line $F_5$ to form upper and lower sections extending throughout the diaper and with a portion 80 of the section which is devoid of pile being disposed in superposed relation to the surface of the pile area 35h having pile loops 33h thereon. Diaper 30h is secured in folded relation by suitable spaced stitching 81, 82 penetrating through the upper and lower sections immediately adjacent opposite sides of the pile area 35h, and overedge stitching 83 along the side thereof opposite the fold line. The portions of the diaper between the lines of stitching 81, 82 and the side edges of the diaper define pinning panels 36h and 37h.

Therefore, diaper 30h has a portion of the hydrophobic base defining one surface thereof and has the hydrophilic pile disposed interiorly of the central portion thereof. Accordingly, when the diaper is applied to a wearer, the hydrophobic base portion will contact the wearer's skin and will wick the moisture therefrom into the interior of the diaper where the moisture will be absorbed by the hydrophilic pile yarns.

It is therefore believed apparent that a novel pile diaper is provided by the present invention wherein enhanced softness, absorbency and/or wearer comfort are achieved to a greater degree than has heretofore been achieved in diapers. Additionally, diapers of the present invention provide these desired characteristics in the diaper without a reliance upon folding of the diaper to provide a large number of layers in the central portion thereof, pads, inserts or special weaves.

In the drawings and specification there has been set forth preferred embodiments of the invention, and although specific terms are employed, they are used in a generic and descriptive sense only and not for purposes of limitation, the scope of the invention being defined in the claims.

What is claimed is:

1. A diaper adapted to be worn having hydrophilic fibers for the desired absorbency therein and being characterized by a pile area disposed in an intermediate portion of the diaper between non-pile areas, said diaper comprising a base of pliable material, and pile yarns penetrating through a portion of the base and forming raised pile on one surface of said base portion and being interknit and forming stitch loop chains on the other surface of said base portion to anchor the pile yarns in the base, and said pile yarns and base portion defining a pile area disposed in the central portion of the diaper when the diaper is in use.

2. A diaper according to claim 1 wherein said base includes superposed upper and lower sections and said pile yarns penetrate through the medial portion of each of said sections and define raised pile faces on opposite outer surfaces of the diaper for contact with the wearer's skin.

3. A diaper according to claim 1 wherein said base includes a plurality of superposed sections, and said pile yarns penetrate through a portion of one of said sections and form raised pile on one surface thereof, which raised pile is disposed interiorly of the central portion of said diaper.

4. A diaper adapted to be worn having hydrophilic fibers for the desired absorbency therein and being characterized by a pile area disposed in an intermediate portion of the diaper between non-pile areas, said diaper comprising a base of pliable material, and pile yarns penetrating through a portion of the base and having portions thereof formed into pile loops extending above one surface of said base portion to form raised pile thereon, said pile loops being arranged in generally parallel rows on the surface of said base portion, each of said pile loops extending diagonally of said base portion and having leg portions penetrating through said base portion at spaced points, adjacent loops in each of said rows having the leg portions at one side thereof penetrating through said base portion at a common point and the leg portions at the other sides thereof penetrating through said base portion at spaced apart points whereby said pile loops are arranged in a zig-zag pattern in each of said rows with leg portions of the pile loops in one row and the proximal leg portions of the pile loops in the adjacent row being in alignment in a direction longitudinally of the rows to provide substantial coverage of the surface of said base portion, said pile yarns being interknit and forming stitch loop chains on the other surface of said base portion to anchor the pile yarns in the base portion, and said pile yarns and base portion defining a pile area disposed in the central portion of the diaper when the diaper is in use.

5. A diaper according to claim 4 wherein said base is formed of pre-woven textile fabric formed of sets of warp and filling yarns, and wherein said pile yarns have lower twist therein than said warp and filling yarns and provide a soft pile face on said base portion.

6. A diaper according to claim 4 wherein said base is formed of a non-woven fabric.

7. A diaper according to claim 4 wherein said base is formed of a pre-knitted fabric.

8. A diaper according to claim 4 wherein said pile yarns consist essentially of cellulosic material and have a yarn size within the range of 3/1 to 20/1 and a twist multiple of no more than 3.5 to provide a soft, highly absorbent pile in the central portion of the diaper when the diaper is in use.

9. A diaper adapted to be worn characterized by an intermediate portion having a pile face on one surface thereof said diaper having hydrophilic fibers therein for the desired absorbency and comprising a base of at least one layer of textile fabric, and pile yarns penetrating through an elongate intermediate portion of the base and having portions thereof extending above and substantially covering one surface of said intermediate base portion to form a raised pile face thereon, said pile yarns being interknit and forming stitch loop chains on the other surface of said intermediate base portion to anchor the pile yarns therein, said intermediate base portion extending throughout one dimension of said diaper and having a width of about one-half the other dimension of said diaper and being disposed in the central portion of the diaper when the diaper is in use with the pile face thereon being adapted to be in contact with a wearer's skin, said base including side portions on opposite sides of said intermediate portion and defining pinning panels in the diaper for pinning the diaper on a wearer.

10. A diaper according to claim 9 wherein said base is formed of a plurality of layers of textile fabric and said pile yarns penetrate through all of the layers of the base and secure these layers together in the intermediate portion of the diaper with the layers of the base in said side portions thereof being independent to facilitate the insertion of pins therethrough for ease in pinning the diaper upon a wearer.

11. A diaper adapted to be worn characterized by an intermediate portion having a pile face on at least one surface thereof between non-pile areas, said diaper comprising a base of textile fabric, and low twist, shrinkable pile yarns consisting essentially of cellulosic fibers having a tendency to mat under laundering conditions and penetrating through an intermediate portion of the base and having portions thereof extending above and substantially covering one surface of the intermediate base portion to form a raised pile face thereon, said pile yarns being interknit and forming stitch loop chains on the other surface of the base to anchor the pile yarns in the base, the shrinkability and twist of said pile yarns effecting rearrangement of the pile face into a closely matted surface upon repeated launderings to provide more complete coverage of said intermediate base portion, and the intermediate base portion having the pile face thereon being disposed in the central portion of the diaper when the diaper is in use.

12. A diaper adapted to be warn characterized by an intermediate portion having a pile face on at least one surface thereof, said diaper comprising a base of pliable material, and pile yarns penetrating through an intermediate portion of the base and having portions thereof extending above one surface thereof to form a raised pile face thereon, said pile yarns being interknit and forming stitch loop chains on the other surface of said intermediate base portion to anchor the pile yarns therein, certain portions of said pile face being formed of hydrophobic material and other portions thereof being formed of hydrophilic material, said hydrophobic portions being arranged to define at least the outermost surface of said pile face adapted to contact the skin of a wearer and to wick moisture away from the wearer's skin, said hydrophilic portions being arranged relative to said hydrophobic portions to absorb the moisture being wicked away from the skin of a wearer by said hydrophobic portions, and the intermediate base portion having said pile face thereon being disposed in the central portion of the diaper when the diaper is in use with the pile face being adapted to be in contact with the wearer's skin.

13. A diaper according to claim 12 wherein said hydrophobic portions of said pile face are defined by pile of a predetermined height and said hydrophilic portions are defined by pile of a lesser height than said hydrophobic pile.

14. A diaper according to claim 12 wherein said pile yarns comprise core-spun yarns each having a hydrophilic core and a hydrophobic sheath of fibers around said hydrophilic core, said hydrophobic sheaths of said pile yarns defining said hydrophobic portions of said pile face and said hydrophilic cores of said pile yarns defining said hydrophilic portions of said pile face so that moisture is wicked to the interior of said pile yarns by said hydrophobic sheaths and is absorbed by said hydrophilic cores away from the wearer's skin.

15. A diaper adapted to be worn characterized by an intermediate portion havig a pile face on at least one surface thereof, said diaper comprising a base of pliable material, and pile yarns penetrating through an intermediate portion of the base and having portions thereof formed into the pile loops extending above one surface of said intermediate base portion to form a raised pile face thereon, said pile loops being of different heights with the higher pile loops being formed from pile yarns of hydrophobic material and the lower pile loops being formed of hydrophilic material and being interspersed with said hydrophobic pile loops over substantial areas of the pile face, said pile yarns being interknit and forming stitch loop chains on the other surface of said intermediate base portion to anchor the pile yarns therein, and said intermediate base portion having the pile face thereon being disposed in the central portion of the diaper when the diaper is in use with the pile face being adapted to be in contact with the skin of a wearer so that moisture will be wicked away from the wearer's skin by said higher hydrophobic pile loops and absorbed away from the wearer's skin by said lower hydrophilic pile loops.

16. A diaper according to claim 15 wherein said pile loops are arranged in generally parallel rows on the surface of said intermediate base portion, with said hydrophobic pile loops defining certain rows, and said hydrophilic pile loops defining certain other rows interspersed therewith.

17. A diaper adapted to be worn characterized by an intermediate portion having a pile face on at least one surface thereof, said diaper comprising a base of pliable material, and pile yarns penetrating through an intermediate portion of the base and having portions thereof extending above one surface thereof to a common height to form a raised pile face thereon, certain of said pile yarns being formed of hydrophobic material and the remainder of said pile yarns being formed of hydrophilic material, said hydrophilic pile yarns having a low twist and being contractible upon repeated launderings to effect a reduction of the pile formed by said hydrophobic pile yarns, said pile yarns being interknit and forming stitch loop chains on the other surface of said intermediate base portion to anchor the pile yarns therein, and said intermediate base portion having the pile face thereon being disposed in the central portion of the diaper when the diaper is in use with the pile face being adapted to be in contact with wearer's skin.

18. A diaper adapted to be worn characterized by an intermediate pile portion disposed in the central portion of the diaper when the diaper is in use, said diaper comprising a base of textile fabric and pile yarns penetrating through a portion of the base and forming raised pile on one surface of said base portion and being interknit and forming stitch loop chains on the other surface of said base portion to anchor the pile yarns therein, the remaining portions of said base being devoid of pile, said pile yarns being formed of hydrophilic fibers for absorbency, said base being arranged in a plurality of superposed sections with said base portion penetrated by said pile yarns being disposed in the central portion of the diaper and with a section of said base devoid of pile being disposed in superposed contiguous relation to the raised pile on one surface of said base portion to position said pile interiorly of the central portion of the diaper, and at least said section of the base in superposed contiguous relation to said pile portion being formed of hydrophobic material and being adapted to contact the wearer's skin to wick moisture therefrom into the interior of the diaper for absorption by said hydrophilic pile.

19. A diaper according to claim 18 wherein said base is arranged in three superposed sections in the central portion of the diaper with said pile portion defining the internal section between opposite outer sections devoid of pile which define opposite outer surfaces of the central portion of the diaper, and wherein at least said outer sections of said base are formed of hydrophobic material.

*20. A pliable integrated sheetlike diaper adapted to be worn, including a base of pliable material, hydrophilic fibers incorporated in said diaper providing the desired absorbency therein, said diaper being characterized by a pile area on at least one face thereof extending lengthwise of said diaper and disposed intermediately of two nonpile areas also extending lengthwise of said diaper, said pile area comprising raised pile yarns noncontinuous with any yarns of said base material and formed of yarn loops threaded through other yarn loops.*

References Cited

The following references, cited by the Examiner, are of record in the patented file of this patent or the original patent.

UNITED STATES PATENTS

| | | | |
|---|---|---|---|
| 816,036 | 3/1906 | Peters et al. | 128—284 |
| 2,331,289 | 10/1943 | Amidon | 66—85 |
| 2,890,579 | 6/1959 | Mauersberger | 66—85 |
| 3,113,570 | 12/1963 | Holliday et al. | 128—284 |
| 3,224,446 | 12/1965 | Gore | 128—284 |
| 3,253,426 | 5/1966 | Mauersberger | 66—85 |

FOREIGN PATENTS

| | | |
|---|---|---|
| 10,928 | 1897 | Great Britain. |

CHARLES F. ROSENBAUM, Primary Examiner